US006736792B1

(12) United States Patent
Liu

(10) Patent No.: US 6,736,792 B1
(45) Date of Patent: May 18, 2004

(54) NASAL-NASOPHARYNGEAL-CLEANING SYSTEM

(76) Inventor: James Zhou Liu, 462 Burns Dr., Westerville, OH (US) 43082

( * ) Notice: Subject to any disclaimer, the term of this patent is extended or adjusted under 35 U.S.C. 154(b) by 280 days.

(21) Appl. No.: 09/598,522

(22) Filed: Jun. 21, 2000

Related U.S. Application Data

(63) Continuation-in-part of application No. 09/071,459, filed on May 1, 1998, now Pat. No. 6,238,377, which is a continuation-in-part of application No. 08/788,329, filed on Jan. 27, 1997, now abandoned.

(51) Int. Cl.[7] .......................... A61M 31/00; B65D 37/00; B67D 3/00
(52) U.S. Cl. ..................... 604/94.01; 222/211; 222/212; 222/481.5; 222/482
(58) Field of Search ............................. 604/289, 94.01, 604/73, 35, 36, 315, 313, 316; 600/538; 128/207.18, 200.24, 200.11; 606/162, 196, 199; 222/206, 207, 211, 212, 215, 481.5, 482

(56) References Cited

U.S. PATENT DOCUMENTS

| | | | | |
|---|---|---|---|---|
| 1,248,891 A | | 12/1917 | Nichols ....................... 604/289 |
| 1,487,252 A | | 3/1924 | Lore .......................... 604/289 |
| 1,502,163 A | * | 7/1924 | Sprague ...................... 604/217 |
| 2,566,806 A | | 9/1951 | Miller ........................ 128/173 |
| 2,582,529 A | * | 1/1952 | Curry ..................... 128/200.18 |
| 2,693,800 A | | 11/1954 | Caldwell ..................... 604/289 |
| 3,847,145 A | * | 11/1974 | Grossan ...................... 601/160 |
| 4,029,095 A | | 6/1977 | Pena ......................... 128/250 |
| 4,403,611 A | * | 9/1983 | Babbitt et al. .............. 604/118 |
| 4,980,163 A | | 12/1990 | Blackburn et al. ........ 434/94.63 |
| 5,116,311 A | | 5/1992 | Löfstedt ...................... 604/54 |
| 5,183,467 A | | 2/1993 | Mouney ...................... 604/140 |
| 5,314,690 A | * | 5/1994 | Patterson et al. ............ 424/114 |
| 5,505,193 A | | 4/1996 | Ballini et al. ................ 128/200 |
| 5,752,510 A | * | 5/1998 | Goldstein ............... 128/200.24 |
| 5,794,619 A | * | 8/1998 | Edelman et al. ........ 128/200.24 |
| 6,238,377 B1 | * | 5/2001 | Liu ............................ 604/289 |

FOREIGN PATENT DOCUMENTS

GB    2 082 462 A    3/1982

OTHER PUBLICATIONS

A publication entitled: "Ephedrine–saline nasal wash in allergic rhinitis", in *J. Allergy Clin. Immunol.*, by Wiqar A. Shaikh, M.D., Nov., 1995 p. 597–600.
A publication entitled: "Parainfluenza viral infections in children: Correlation of shedding with clinical manifestations" by Hall et al. in *The Journal of PEDIATRICS*, vol. 91, No. 2, pp. 194–198.
A publication entitled "Clinically Useful Method for the Isolation of Respiratory Syncytial Virus" by Hall et al. in *The Journal of Infectious Diseases*, vol. 131, No. 1, Jan., 1975, pp. 1–5.
A publication entitled: "Quantitative Shedding Patterns of Respiratory Syncytial Virus in Infants" by Hall et al. in *The Journal of Infectious Diseases*, vol. 132, No. 2, Aug., 1975, pp. 151–156.

* cited by examiner

*Primary Examiner*—Weilun Lo
*Assistant Examiner*—Linh Truong
(74) *Attorney, Agent, or Firm*—Standley Law Group LLP

(57) ABSTRACT

A nasal-nasopharyngeal-cleaning (NNC) system is disclosed for removing harmful substances from a human's nasal and nasopharyngeal cavities. Harmful substances herein include infectious agents, chemicals, dust, small particles and dirt deposits in nasal cavities and in the nasopharynx. The NNC system includes a NNC solution, a solution container, a liquid transfer tube, a valve means and a flat-head nostril fitting. The two-step cleaning process comprises cleaning the nasal cavity first with the NNC system and then cleaning the nasopharyngeal cavity with the NNC system. The NNC system is also used to prevent snore.

7 Claims, 4 Drawing Sheets

The Portable NNC System

Figure 1:
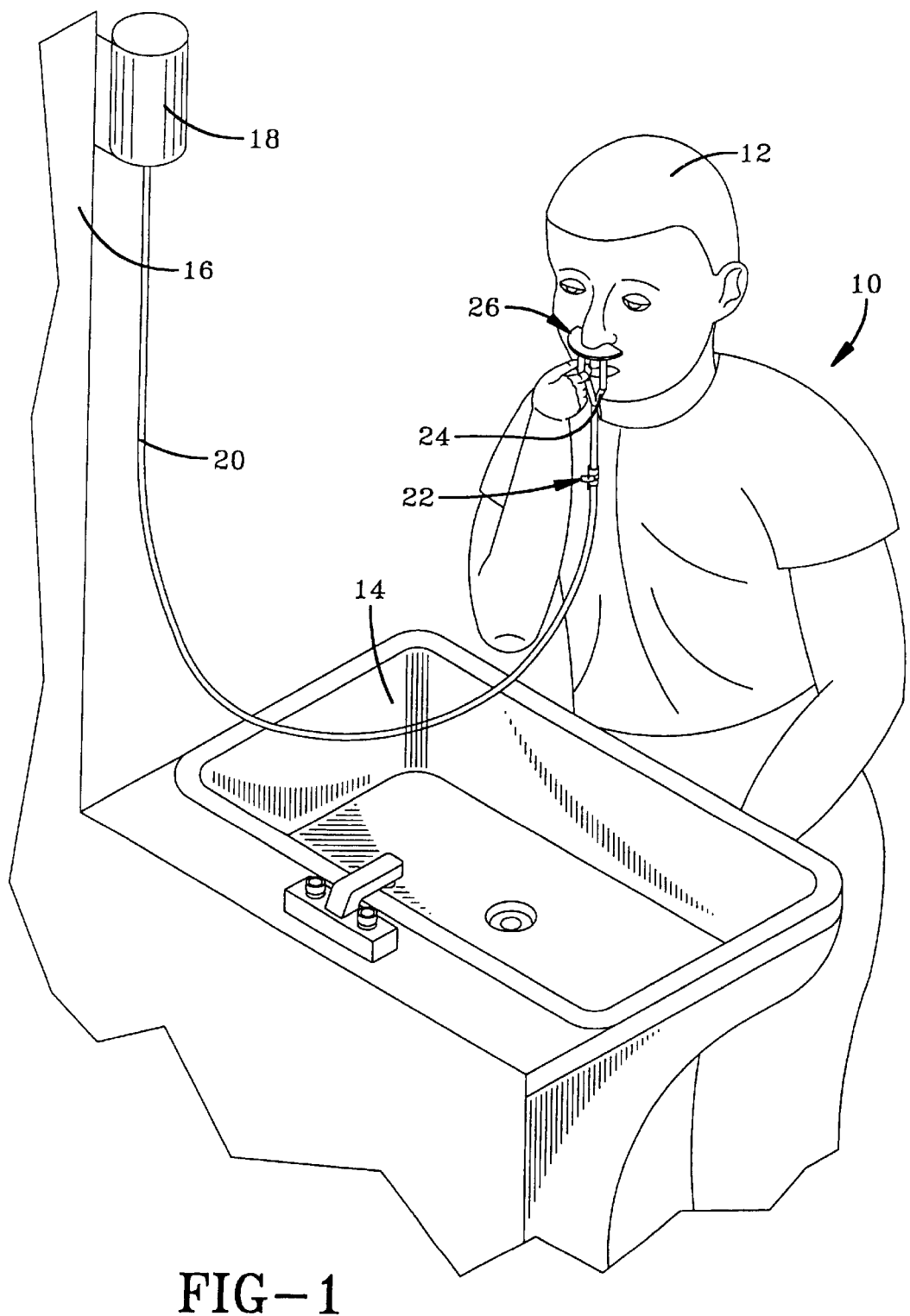

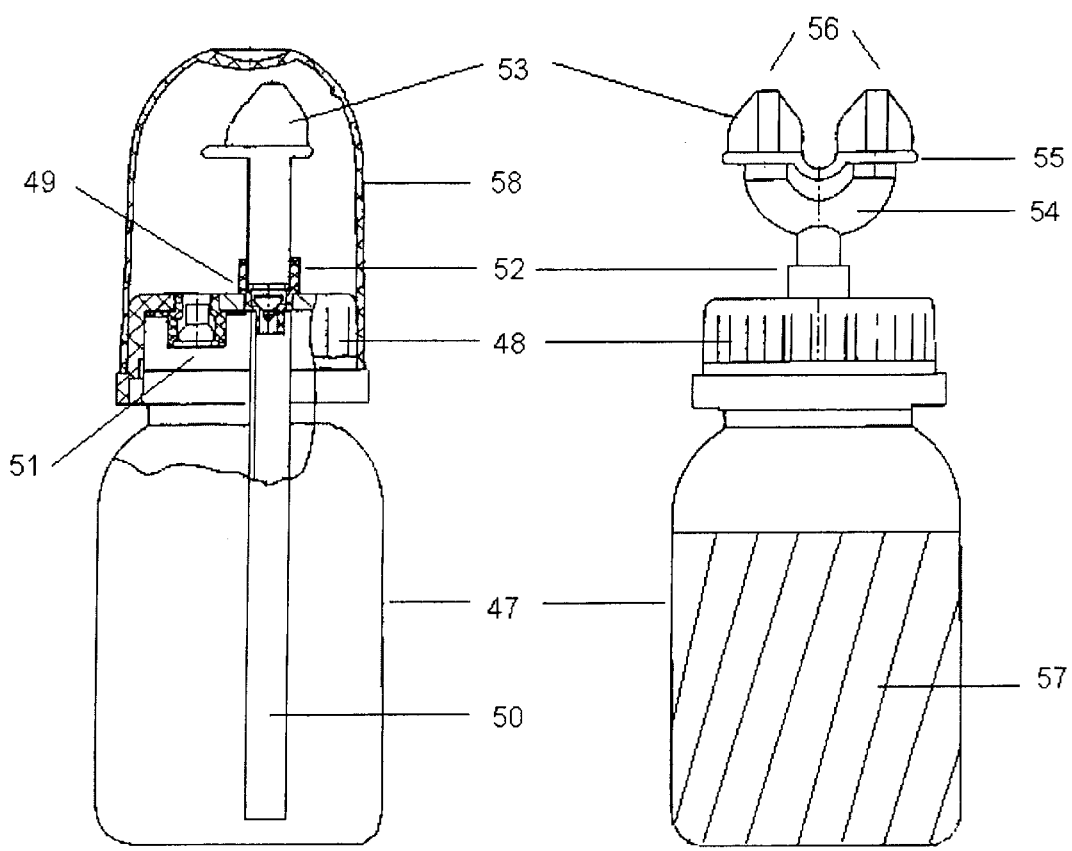
FIG - 6. The Portable NNC System
FIG - 7. The Portable NNC System

NASAL-NASOPHARYNGEAL-CLEANING SYSTEM

RELATED APPLICATIONS

This application is a continuation-in-part application of U.S. Ser. No. 09/071,459, filed on May 1, 1998, now U.S. Pat. No. 6,238,377, issued May 29, 2001, which itself is a continuation-in-part application of U.S. Ser. No. 08/788,329, filed Jan. 27, 1997, now abandoned.

TECHNICAL FIELD OF THE INVENTION

The present invention relates generally to a nasal-nasopharyngeal-cleaning (NNC) system to be used in removing harmful substances from a human's nasal and nasopharyngeal cavities. Harmful substances include infectious agents, chemicals, dust, solidified mucous and dirt which adhere to the nasal cavities and the nasopharynx. The NNC system of the present invention comprises the NNC solution and its container, a liquid transferring system, and a flat-head nostril fitting which optionally comprises a means for holding the nostril fitting against the nostrils. A two-step method of using the NNC system is also provided.

BACKGROUND OF THE INVENTION

Influenza viruses A, B and C; respiratory syncytial viruses A and B; parainfluenza viruses and the like are common causes for respiratory tract infections in humans. Presently, there are no effective drugs or vaccines to treat or prevent these viral infections. Human adults and school children are constantly exposed to these infectious agents at work and/or at school and may also be carriers of these infectious agents to and from the home. A practice of nasal and nasopharyngeal cleaning may reduce the microbial load of those tissues and reduce the chance of spreading these disease-causing microorganisms at home, school and at work.

Many disease-causing agents exist in the nasal and nasopharyngeal cavities. The shedding of communicable infectious microorganisms in the nasal and nasopharyngeal cavities causes spreading of the disease from the upper respiratory tract to the lower respiratory tract of the carrier. Shedding also causes the spreading these infectious agents to other people through sneezing and/or coughing (Hall, C. B., Douglas, R. J., in an article entitled: "Quantitative shedding patterns of respiratory syncytial virus in infants", *Journal of Infectious Diseases*, 132: 151–156, 1975; and Hall, C. B., Geiman, J. M., Breese, B. B., and Douglas, R. J., in an article entitled "Parainfluenza virus infections in children: Correlation of shedding with clinical manifestations", *Journal of Pediatrics*, 91: 194–198, 1977). For most viral infections, antibiotic prevention and/or treatment is generally ineffective. It would thus be beneficial to have a practical system and/or method to remove these disease-causing agents from the human body. In a manner similar to brushing one's teeth, nasal and nasopharyngeal cleaning in the general population will have a number of healthy benefits.

Nasal washes, nasopharyngeal swabbing and nasopharyngeal aspiration have previously been used to obtain specimens from patients for the determination of microbial pathogens (Hall, C. B., Douglas, R. J., in an article entitled: "Clinically useful method for the isolation of respiratory syncytial virus", *Journal of Infectious Diseases*, 131: 1–5, 1975). However, these procedures and devices were used only to obtain samples and are not effective in removing the infectious agents from the nasal and nasopharyngeal cavities of a human.

Ephedrine nasal washes have been used in the treatment of sinusitis and other nasal and paranasal symptoms and allergic rhinitis (Shaikh, W. A., in the *Journal of Allergy Clinical Immunology*, Vol. 96, No. 5, part 1: 597–600, 1995). The Shaikh procedure uses a 1% ephedrine hydrochloride solution in a normal saline solution and a Higginson's rubber syringe. After the rubber syringe was filled with the wash solution, the nozzle of the syringe was introduced into nostril and the bulb of the syringe was passed to push the fluid into the nasal cavity. As described by the author, most of the fluid exited from the same nostril, but some fluid exited through the other side of the nose after passing through the nasopharynx. This procedure was performed once every forty-eight (48) hours for a four (4) week period and caused a significant improvement in symptom scores and peak nasal inspiratory flow rates in patients with perennial allergic rhinitis as compared to those treated with a placebo wash (normal saline only). This procedure, however, has the following disadvantages:

(1) ephedrine was the key factor for the effectiveness of this procedure, but this chemical is not suitable for use by the general public on a daily basis;

(2) this procedure was performed only on patients with perennial allergic rhinitis;

(3) this procedure was mainly washing of the nasal cavity, the nasopharyngeal cavity was largely uncleaned;

(4) the apparatus used was clumsy and uncomfortable to use; and (5) this procedure was performed once every forty-eight (48) hours which is not frequent enough to remove harmful materials from the nasal and nasopharyngeal cavities on a daily basis.

The Shaikh procedure would permit the infectious microorganisms to be brought into and spread around at home, office, school, or day care center. Therefore, there is a need to develop a generally acceptable and more effective nasal and nasopharyngeal cleaning system.

Nasal and nasopharyngeal cavities are common places for holding environmental allergens, such as pollen, fungal spores, animal body-originated dustings and volatile chemicals. These harmful agents cause allergic reactions and other ill consequences. Nasal and nasopharyngeal secretions combine with environmental particles to form big matters (solidified mucous) in the nasal cavity. These big matters narrow the airway and make the individual feel uncomfortable. Prior to the present invention, an aparatus and method to easily and effectively remove harmful agents from the nasal cavity and to prevent the formation of and remove the big matters in the nasal cavity has not been available to medical professionals and to the general public.

The human body is the only natural host for many kinds of pathogenic microorganisms. Nasopharyngeal mucous is one of the prominent places of viral shedding. These pathogens include, but are not limited to, influenza viruses, respiratory syncytial viruses and the like. The nasopharyngeal shedding of these pathogens is the major cause of person-to-person transmission. One skilled in the art will appreciate that those communicable pathogenic microorganisms present in the nasal and nasopharyngeal cavities will be decreased in quantity after the cavities have been cleaned. After nasal and nasopharyngeal cleaning, these infectious agents will be less likely to spread horizontally to non-carriers and/or vertically to the lower respiratory tract of the carrier.

Environmental pathogens may be encountered by inhalation. *Legionella pneumophila*, the causative agent of Legionnaire's disease presents in aerosols. It is generated from air conditioning cooling towers, cold water taps, showers and other water systems. Depending upon wind speed, *Legionella pneumophila*, in these aerosols, may be carried up to 500 meters and infect a large number of individuals. Promptly removing these aerosols from the nasal and nasopharyngeal cavities will greatly reduce the incidence of infection.

Several methods have been reported to be useful in cleaning nasal and nasopharyngeal cavities. Grossan invented a nasal irrigation system (NASAL IRRIGATION SYSTEM, U.S. Pat. No. 3,047,145, issued Nov. 12, 1974) which provided for an isotonic saline solution under pressure flowing into one nostril, passing through the nasolacrimal duct, where the solution passes, sequentially, into the ostia of the frontal sinus, the ethnoids, the maxillary and the sphenoid. The solution then moves past the outlet of the eustachian tube and then through the nasopharynx to the upper posterior portion of the other nostril and outwardly therethrough, passing the same ducts and ostia, in reverse sequence, before being discharged from the second nostril. This system has numerous and serious shortcomings. First, the cleaning solution cannot be completely drained from the deep regions of certain sinuses due to their cavity structure. Second, certain infectious agents might be moved from one place to another and stay there to cause a new infection. Third, some dried or hard matters in the nasal cavity might be carried inward to the sinuses. Fourth, hard matters might cause a blockage when they are forced to flow into narrow spaces, such as the eustachian tube. Therefore, the reported nasal irrigation system of Grossan cannot be widely used by the general public for cleaning nasal and nasopharyngeal cavities.

A method of administrating a pharmacological solution into the nasal cavity of a patient was described by Löfstedt (METHOD FOR DRUG ADMINISTRATION, U.S. Pat. No. 5,116,311, issued May 26, 1992). Although the author mentioned that there was a possibility to use the reported method to irrigate the nasal cavity, the method and device of this patent were designed to administer pharmacological solutions into the nasal cavity, not to provide a flow of fresh cleaning solution continually into the nasal cavity, since the compressible container of Löfstedt not only forced the solution into the nasal cavity, but also aspirated the solution with nasal secretions and other contaminants back into the container. The effectiveness of the drug administration method was also heavily dependent on the patient's head bending angle. This method and device was designed to administer drugs into the nasal cavity for treating diseases over a short period of time. The Löfstedt device was not designed for and would not be useful to clean nasal and nasopharyngeal cavities by the general public on a daily basis.

Pena invented a device for treating infections of the nasal fossae (DEVICE FOR CIRCULATING TREATING FLUID THROUGH THE NASAL FOSSAE, U.S Pat. No. 4,029,095 issued Jun. 14, 1977). The Pena device was designed to be used by patients to treat diseases, not for the general public to clean nasal and nasopharyngeal cavities.

Babbitt et al. invented a portable device used to aspirate and remove fluids from nasal and sinus cavities (SINUS EVACUATOR APPARATUS, U.S. Pat. No. 4,403,611 issued Sep. 13, 1983). Since this device only aspirates the sinus fluids from the nasal and sinus cavities, the dirts and pathogenic microorganisms adhering to the surface of the nasal and nasopharyngeal cavities cannot be removed if they are not dissolved in a washing fluid.

The above systems and methods described in Grossan, Löfstedt and Babbitt et al. all utilize a conical nostril fitting. The conical nostril fitting creates a certain amount of "dead space" between the inserted part of the nostril fitting and the wall of the nasal cavity, which a cleaning solution cannot reach (if used in the Grossan et al. devices). To improve the efficiency of nasal cleaning, a new type of nostril fitting is needed. The prior art has failed to suggest a NNC system that is simple in construction and easy to use and that allows for the cleaning of the nasal and nasopharyngeal cavities in the separated steps. Since the nasal cavity: (1) is naturally in the lowest position as compared to the nasopharyngeal cavity and the other sinus cavities; (2) collects secretions from other sinus cavities; and (3) is the first place to meet and store the foreign matters, it is obvious that the first step of the nasal and nasopharyngeal cleaning method should be to initially clean the nasal cavity. Therefore, a new step-by-step cleaning method is disclosed in this invention.

Snoring is a major problem for many people. In fact, in the U.S. alone, about 90 million people suffer with snoring. This figure doesn't take into consideration the needless suffering of the loved ones living with them. Sleep deprived nights lead to irritation, tiredness, and a possible growing division or alienation between partners. Seeking a simple and effective solution honoring has been a major concern for a large number in our society. Snoring has become an everyday occurrence. It is much more common than many care to admit. Each nostril functions independently and synergistically in filtering, warming, moisturizing, dehumidifying, and smelling the air. The nostrils meet at the nasopharynx where mucous is accumulated. Although many factors cause snoring, the major reason may be that the nasal cavity is narrowed due to accumulated mixtures of mucous and environmental dusts. Habitual nasal cleaning will remove those accumulated dirty materials and help people to reduce snoring.

BRIEF DESCRIPTION OF THE DRAWINGS

These and other objects of the present invention will be apparent to those skilled in the art from the following description of the invention. The invention is described with reference to the following Figures:

FIG. 1 is a perspective view of a person using one embodiment of the NNC system of the present invention, shown leaning over a lavatory or washbasin, and holding the inventive device to the bottom of his nose;

FIG. 2 shows a frontal plan view of one embodiment of the flat-head nostril fitting, "Y" fitting (fluid division means) and handle;

FIG. 3 is a top plan view of one embodiment of the flat-head nostril fitting, the handle being shown in dotted lines;

FIG. 4 is a perspective view of one embodiment of the flat-head nostril fitting wherein the fluid division means (in this embodiment, a "T" fitting) is embedded in the flat-head nostril fitting; and FIG. 5 is a perspective view of one embodiment of the flat-head nostril fitting with a valve means disposed between the "Y" fitting and the NNC solution container (not shown).

FIG. 6 is a perspective view of one embodiment of an assembled portable NNC system.

FIG. 7 is a perspective view of one embodiment of the type of valves that may be used with the present invention.

DETAILED DESCRIPTION OF THE DRAWINGS

In FIG. 1, there is indicated generally at 10 a patient using one embodiment of the NNC system. It will be noted that the patient's body is bent so that his head 12 is slightly bent over a conventional lavatory or washbasin indicated generally at 14 for receiving the discharge of the NNC solution from a nasal cavity. Adjacent to the washbasin 14, and here shown as mounted on a wall 16, is a container 18 of NNC solution. The solution is fed by gravity through a flexible hose 20 which is connected to a valve means 22 which is then connected to the fluid division means fitting 24 (here shown as a "Y" fitting). The "Y" fitting is in connective relationship to the flat-head nostril fitting 26. FIG. 1 shows the patient's right hand holding the flat-head nostril fitting 26 to the underside of the patient's nostrils through holding the handle 42 shown in FIG. 2.

Figure 2:
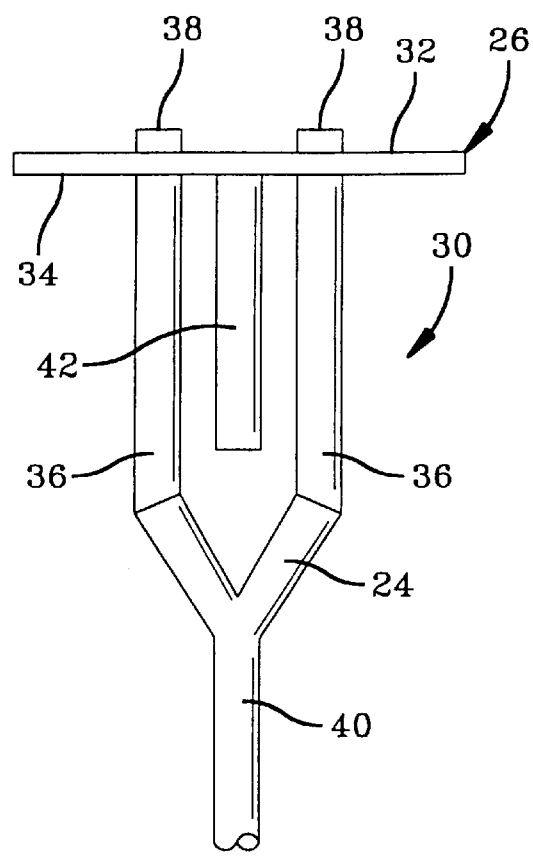

FIG. 2 indicates generally at 30 one embodiment of the NNC system wherein the flat-head nostril fitting 26 has upper surface 32 and lower surface 34. The flat-head nostril fitting is connectively engaged with the fluid division means shown here as a "Y" fitting 24. The two arms of the "Y" fitting 36 extend through the flat-head nostril fitting 26 to create projections 38 above the flat-head nostril fitting upper surface 32. The fluid transfer tubing 40 is in connective engagement with container 18 (not shown). Handle 42 extends from the lower surface 34 of the flat-head nostril fitting 26.

Figure 3:
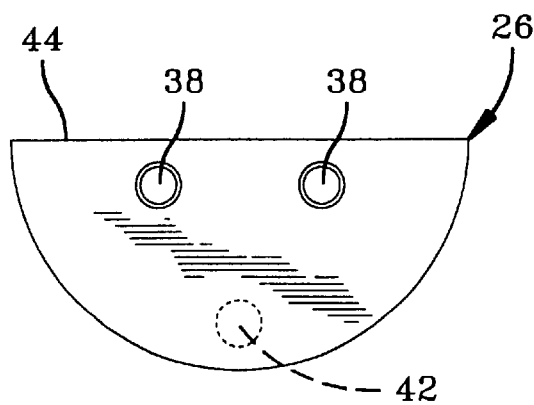

FIG. 3 is a top plan preview of one embodiment of the flat head nostril fitting 26. In this embodiment, the flat-head nostril fitting is generally semi-circular in shape. The straight edge 44 of the flat-head nostril fitting 26 is intended for engagement against the patient's upper lip. Projections 38 result from the extension of the arms of the fluid division means through the flat-head nostril fitting. The spacing of projections 38 relative to straight edge 44, and to one another are such that most human beings upon placement of a device against their upper lip, will find projections 38 inserted into each nostril. While this embodiment is semi-circular in configuration, it should be understood that other shapes such as squares, rectangulars, triangles, hexagons and the like may also be used. The feature of the flat-head nostril fitting that is most critical is that straight edge 44 be of sufficient length and configuration so that proper sealing of the nostrils may be accomplished with top surface 32 of the flat-head nostril fitting 26 while projections 38 enter each nostril of the patient.

Figure 4:
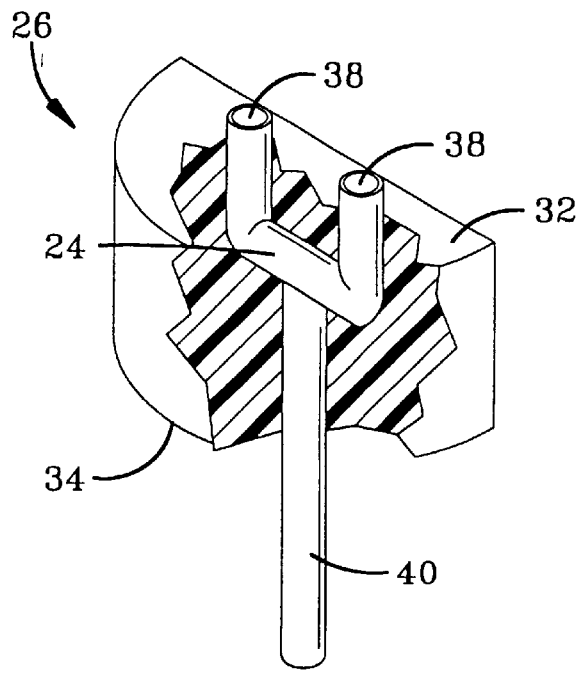

FIG. 4 is a perspective view in partial cross section of yet another embodiment of the invention wherein the fluid division means 24, seen here as a "T" fitting, is embedded within the flat-head nostril fitting 26. The nostril fitting in this embodiment possesses top surface 32 with projections 38 extending therefrom. Bottom surface 34 of the flat-head nostril fitting 26 may have a handle means adapted thereto (not shown). The tubing 40 is connected to a valve means (not shown).

Figure 5:
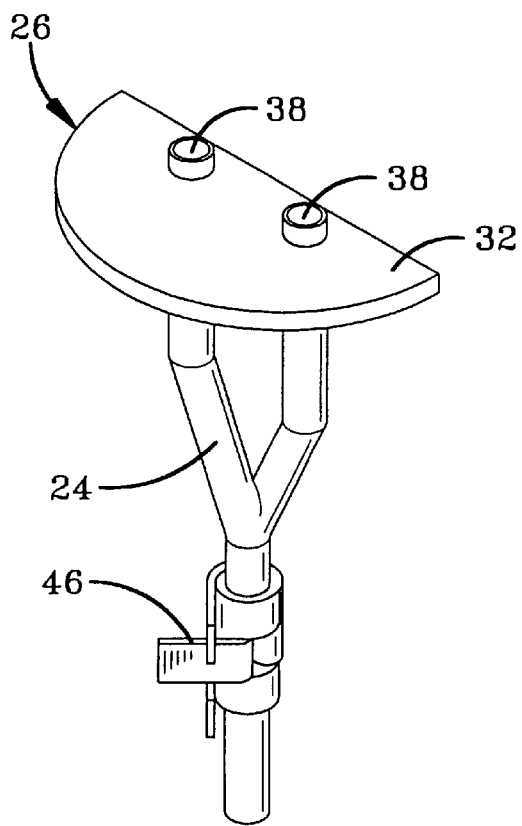

FIG. 5 is a perspective view of another embodiment of the NNC system wherein the flat-head nostril fitting 26 possesses projections 38 through its top surface 32. The fluid division means 24, shown here as a "Y" fitting, is connectively engaged with a valve means 46. This valve means may be any valve type known in the art and may be a squeeze type or push/pull type valve known to those in this field. Other valve means would include those associated with enteral nutrition feeding sets wherein a clamp flow regulator on the tubing permits easy, accurate flow rate adjustment. Preferably, the valve means 46 is configured such that it is closed in normal position and that only upon manual activation would the valve be open, allowing NNC solution to flow from the container 18 through tubing 20 into "Y" fitting 24 through projections 38 and into the nostrils of the patient.

FIG. 6 is a sectional view of one embodiment of the portable NNC system and FIG. 7 is a perspective view of one embodiment of the assembled portable NNC system. The solution container 47 is a soft bottle which may be hand-squeezed to produce pump-like pressure. The container has a unique cap 48. The cap has two valves. One valve is a one-directional fluid-flow switch 49. This liquid-flow switch only allows the cleaning fluid to flow out of the bottle and prevents the dirty washout from flowing into the bottle. The two ends of this fluid-flow valve connect to two different solution transfer tubes. Tube one is a short tube 50 contained within the bottle which transfers the cleaning solution to the nostril fitting leaving the bottle. Tube two connects to the "Y" shaped nostril fitting 54 through a sliding-connector 52. The nostril fitting 53 is an oval object which is used to broaden or narrow the space between the two nostril fittings after moving then around the supporting stem 56. The two supporting stems 56 are short and are in a fixed or movable position on the Y shaped nostril fitting. The nostril fitting has a "one-size-fits-all" adjustability. The second valve on the bottle's cap is a one-directional airflow switch 51. This valve only allows air to flow into the bottle, which allows the bottle to always have positive pressure to make it easier to pump out the cleaning fluid from the container. The cap 58 is to prevent the nostril fittings and valves from gathering dust. The cleaning solution 57 flows through a short tube 50, arrives to the one-directional fluid-flow valve, and fills the nostril fittings to irrigate the user's nasal and nasopharyngreal cavities.

SUMMARY OF THE INVENTION

The present invention provides a nasal and nasopharyngeal cleaning (NNC) system which is used to reduce the load of disease-causing agents; to reduce the concentration of infectious agents in the nasal and nasopharyngeal secretions; to prevent these infectious agents from presenting in aerosols/droplets; and to reduce the duration of environmental allergens and other harmful materials staying in nasal and nasopharyngeal cavities. The NNC system includes a washing solution and its container, a liquid transferring tube system and an all-purpose nostril fitting. The NNC system of the invention is portable and constructed of readily available and inexpensive materials. The NNC system is to be used in a method wherein the nasal cavity is cleaned first and then the nasopharyngeal cavity is cleaned thereafter. The method disclosed for using the NNC system may be applied by an individual to himself or herself as often as required or deemed convenient.

Thus, there is disclosed a nasal and nasopharyngeal-cleaning (NNC) system comprising a NNC solution, a container for said NNC solution, a tubing system, a valve means and a one-fits-all nostril fitting. The NNC system may additionally comprise a fluid division means between the valve means and the one-fits-all nostril fitting. The fluid division means may take the form of a "Y" fitting, a "T" fitting and the like. Numerous variations are possible. The fluid division means may be disposed within the flat-head nostril fitting. The portable NNC system has a unique mechanism which only allows cleaning fluid and air to flow in a designated direction.

There is further disclosed a nasal and nasopharyngeal cleaning (NNC) system for use by a patient comprising:
1) a container with a volume of at least 10 ml connected via tubing to a valve means;
2) said valve means being in the closed position nominally and open upon manual actuation;

3) said valve means connected via tubing to a fluid division means, wherein said fluid division means is selected from "Y" fittings and "T" fittings;

4) said fluid division means passing through a one-size-fits-all nostril fitting, said one-size-fits-all nostril fitting comprising a handle and two openings for passage of said fluid division means;

5) said flat-head nostril fitting comprising at least one curved edge for engagement with the upper lip of said patient and said two openings being positioned relative to said curved edge and to each other such that said fluid division means passing through said opening will insert into the nostrils of said patient.

DETAILED DESCRIPTION OF THE INVENTION

The present invention provides a new nasal and nasopharyngeal cleaning (NNC) system and a method of cleaning the nasal and nasopharyngeal cavities. In general, the NNC system comprises:

(1) a nasopharyngeal cleaning solution comprising at least 0.9 gms of NaCl per 100 ml of water;

(2) a container for said NNC solution, said container comprising a hanging means and a means for connection to tubing;

(3) a valve;

(4) a fluid division means; and (5) a flat-head nostril fitting comprising a handle and one or two openings.

The NNC solution is supplied to the nostril fitting through the force of gravity, by a manual and/or mechanical pump, or provided manually through a squeezable soft bottle. In the embodiment where a pump is used, the pump may be a motor driven pump unit, preferably driven by way of a suitable micromotor. However, the pump means may also be a manually operable pump means in the form of an elastic bulb capable of being manually compressed, and capable of expanding when released by the operator; this particular pump means having at its suction inlet and pressure outlet, respectively, a pair of one way valves which permit the fluid to flow only from the suction tubular means into the plastic bulb when the latter expands and from the elastic bulb only into the pressure tubular means when the elastic bulb is compressed by the operator.

The NNC solution useful in the system and method according to the current invention may be water or an aqueous solution. The most common isotonic solution is a normal saline solution, which contains 9 g of sodium chloride in 1 liter of water (0.9% by weight). This solution may be used as a basal cleaning solution. It has been experienced that a phosphate buffered water solution (pH 7.4) containing sodium chloride at a concentration higher than 0.9% normal saline, resulted in a more comfortable nasal and nasopharyngeal cleaning. Thus, a phosphate buffered aqueous solution containing about 1 g of sodium chloride per 100 mL water is a preferred NNC solution. The NNC solution may also contain an appropriate amount of an anti-attachment agent. Representative anti-attachment agents include various carbohydrates or detergents which prevent or reduce the attachment of microbial pathogens to the nasal and nasopharyngeal cavities. The solution may also contain anti-allergy agents, or suitable detergents to improve the cleaning efficiency. The NNC solution may also contain corticosteroids, antibiotics, antihistamines, and/or mucolytic agents. The NNC solution may also contain a suitable decongestant such as phenylephrine hydrochloride. Pharmaceutically active agents should be employed in the NNC solution only under the direction of a physician. The temperature of the NNC solution, when administered, is typically about 20 to 40° C. and more preferably about 30 to 37° C.

The container for NNC solution may be made of any convenient material and may take almost any shape. The container may hold up to 50,000 mL of solution, preferably it may hold 10 to 10,000 mL of solution and more preferably, it may hold at least 50 mL of NNC solution. This container may be made from any kind of safe material which does not release any chemicals into the solution and does not absorb any chemicals from the solution. The common materials include, but are not limited to, plastic, rubber, glass, metals, china, etc. One end of the container preferably has a means to hang the container above the head of the patient and the other end is open with means to be connected to the tubing system. The container may be a soft bottle to produce fluid-flow force when manually squeezed.

A flexible tubing system is used to transfer the NNC solution to the flat-head nostril fitting and into the patient. The tubing may be from 30 cm to 2 meters in length. Preferably, it is between 0.5 to 1 meter in length. The inner diameter of the tubing is between 2 to 10 mm. Preferably, the inner diameter is between 3 and 7 mm. The material of the tubing may include, but is not limited to, plastic, rubber or any other suitable inert material. One end of the tubing is connected to the container of the NNC solution and the other end is connected to the valve means. If a portable NNC system is made, the tubing system will become a within-bottle short tube.

Disposed between the NNC container and the flat-head nostril fitting is a valve and a fluid division means. The valve allows the patient to control the flow of NNC solution from the container, through the nostril fitting and into his or her nasal cavity. In a preferred embodiment, the valve, which may be of any known and convenient design, is near to or incorporated into the flat-head nostril fitting as will be further discussed below.

The flexible tubing system may also comprise a fluid division means such as a "Y" fitting disposed between the valve means and the nostril fitting. The "Y" or "T" fitting takes the NNC solution and divides it so that each nostril is afforded simultaneous essentially equal irrigation. In one embodiment of the invention, the "Y" or "T" fitting is integrated into the flat-head nostril fitting.

The two arms of the fluid division means may have the same diameter enabling the smooth connection of the tubing system to the nostril fitting. The connection between the tubing, the valve and the nostril fitting may be formed by contraction force of the elastic tubing or by a plastic or metal screw connection. The combination of the NNC container, the tubing system, the valve and the connections are similar to the apparatus used in hospitals for intravenous infusion or the apparatus for gastric tube feeding. When a portable NNC system is made, the container, the tubing system, the valves and the connections are similar to a small liquid sprayer.

One important aspect of the NNC system according to this invention is the flat-head nostril fitting, or one-size-fits-all nostril fitting. The nasal fitting substantially prevents the NNC cleaning solution from leaking from the nostril during the irrigation step of the process. It has been observed that different people have different shaped nostrils and that not all people have round nostrils. Some people have an irregular opening, like a long narrow channel. Therefore, it is impossible to use the conical shaped nostril fitting of the prior art to prevent the liquid from leaking from the nostrils of these people. Additionally, the conical shaped nostril fittings of the prior art always create a certain amount of dead space between the inserted part of the nasal fitting and the wall of the nasal cavity. The newly invented nostril fitting, as shown in FIGS. 2–5, is called a "flat-head nostril fitting". The flat-head nostril fitting has the following characteristics in a preferred embodiment:

(1) It has a semi-circle head with a diameter of from 2.0 to 8.0 cm and a thickness of 0.1 to 0.5 cm. The function of the curved edge of the semi-circle (or any other shape) is for placement against the upper lip of the patient. The upper surface of the fitting is placed against the bottom of the nose so as to reduce liquid leakage from the nasal cavity during the cleaning process.

(2) The flat-head nostril fitting has 2 openings therethrough which allow passage of the tubing from the fluid division means. The openings have a diameter which is identical or slightly less than the outside diameter of the tubes penetrating through the head so as to provide for frictional engagement. The distance from the center of one opening to the center of the other opening is from 0.2 to 1.0 cm and is preferably about 0.5 cm so as to match the average distance between the center of each nostril of the patient.

(3) The length of the two tube-arms of the fluid division means is from 5 to 20 cm. A 10 cm or less length is preferred. In another embodiment of the nasal fitting, the fluid division means is embedded in the flat-head nasal fitting, as set forth in FIG. 4. In this embodiment, the thickness of the head is increased to accommodate the fitting. The embedded "T" shaped configuration is preferred so as to keep the thickness of the head to a minimum. When a portable NNC system is made, the two tube-arms of the fluid division means is from 0.5 to 5 cm.

(4) The outside diameter of the tubes penetrating through the nostril fitting head is preferably from 0.2 to 0.5 cm.

(5) The length of the tubing projecting above the nostril fitting head, items 38 in FIGS. 2–5, is from 0.0 to 0.5 cm, preferably 0.1–0.4 cm. The tube will preferably have a diameter smaller than the diameter of the patient's nostrils in a round shape. This is important so as to prevent the creation of any dead space, as discussed above, during the cleaning process.

(6) The nostril fitting may optionally comprise a handle means. While the NNC system is easily used by the patient without a handle means, it has been found convenient for the patient to have some feature attached to the nostril fitting to facilitate holding of the nostril fitting to the bottom of the nose, such as the solution container of a portable NNC system. In one embodiment, the handle means comprises a rod projecting form the bottom surface of the head. The handle may have a diameter of about 1.0 cm and a length of about 2.0 cm. This handle may also be square or rectangular in shape. This handle, no matter of what configuration, is to provide ease for the cleaner to hold the nostril fitting against the nostrils to introduce and to release the NNC solution during the cleaning process.

(7) Plastic, rubber, stainless metal materials or other safe materials may be used to make the flat-head nostril fitting. Soft, biocompatible silicons are preferred.

A driving force for the NNC solution flowing through the NNC system must be provided. Natural gravity force, manual pump, or a mechanical pump may be used to force the NNC solution into the nasal and nasopharyngeal cavities. Preferably, the force used to move the fluid through the tubing to the nostrils is produced by hanging the container of NNC solution at a position of at least 0.1 meter above the patient's forehead. The force to move the cleaning solution into the nostrils may be produced by a hand-squeezable bottle when a portable NNC system is made.

EXAMPLES

Example I

Cleaning of the Nasal and Nasopharyngeal Cavities

The method of using the NNC system is simple and readily accomplished by the patient. The NNC solution was made by dissolving 2.7 g of table salt into 200 ml of warm drinkable water. One minute before use, the solution was measured to be 37° C. 100 ml of this solution was charged to the NNC solution container. The container was suspended form a hook projecting from the wall of the bathroom at about 50 cm above the patient's forehead.

Cleaning was accomplished as follows:

Step 1:

The patient was in an upward position with the upper part of the body bending slightly forward to have the face above the washbasin, similar to a "teeth brushing" position. The patient used one hand to open the valve to allow the NNC solution to flow through the NNC system. The other hand held the flat-head nostril fitting against the bottom of the nose to allow the NNC solution to reach the nasal cavity. After the NNC solution filled the nasal cavity, the patient withdrew the nostril fitting from the bottom of his nose, after closing the valve, to allow the solution combined with the nasal cavity secretions to flow/fall into the washbasin. He repeated this liquid in-and-out process several times. The patient then closed the valve of the NNC system after his nasal cavity was filled with the NNC solution. While one hand held the nostril fitting in position, he used the other hand to gently rub his nose to allow the dried and hard matters to be released from the nasal cavity. Then the washing solution in the nasal cavity was released into the washbasin. He repeated this in-depth cleaning process several times. Through the mirror, he saw his nasal cavity was very clean. The cleaning result was verified by a medical examiner (physician).

Step 2:

Cleaning of the Nasopharyngeal Cavity

The same patient proceeded to the next step in the process; cleaning of his nasopharyngeal cavity. He was in an upward standing position. After his nasal cavity was cleaned, he placed the nostril fitting against his nose and let the NNC solution fill the nasal cavity without releasing it. When the nasal cavity was full of the NNC solution, he bent his head slightly backward to let the solution naturally flow through the nasopharyngeal cavity. The patient felt that there was some liquid in his mouth. When his mouth was filled with a comfortable amount of solution, he turned off the NNC solution supply (closed the valve) and returned his head to the teeth brushing position. The washing solution was then released from the mouth to the washbasin. This process was continued for two (2) minutes. The medical examiner/physician found that the patient's nasopharyngeal cavity was clean. During Steps 1 and 2, the patient did not get any pressure from any sinus cavity, because the liquid did not flow into any of the sinuses above his nose.

Example II

Cleaning the Nasal Cavity by an Adult

The NNC solution contained sodium chloride at a concentration of 1.35% by weight. One minute before use, the NNC solution was measured to be 37° C. The patient added this solution into the NNC solution container. This container was hung from the wall of the bathroom at about 60 cm above the patient's forehead. The patient placed the nasal fitting under his nose. After opening the valve, the NNC solution flowed through the tubing and the nostril fitting and filled the nasal cavities of the patient. The patient removed the nostril fitting to let the solution flow out of his nasal cavities. By repeating this procedure, several big matters were removed from the nasal cavity. This procedure was repeated several times and the patient's nasal cavities were then examined. The medical examiner/physician could not see any dirty materials left in the patient's nasal cavities.

Example III
Cleaning the Nasopharyngeal Cavity by an Adult

The same patient as mentioned in Example II, continued with the method to clean his nasopharyngeal cavity. After cleaning his nasal cavity, he placed the nostril fitting against the nose and allowed the NNC solution to flow through the nasopharyngeal cavity until the solution reached the patient's oral cavity. The patient simply spit this solution into the washbasin. By repeating this procedure, his nasopharyngeal cavity was cleaned. He felt that the air he inhaled was much fresher than before he cleaned his nasopharyngeal cavity.

Example IV
Cleaning Nasal and Nasopharyngeal Cavities by a Child

The washing solution was made and used the same way as set forth in Example I. A nine (9) year old child performed the cleaning process. The procedure took 5 minutes to clean both the nasal and nasopharyngeal cavities. As seen by the medical examiner/physician, no dirty material was left in the child's nasal and nasopharyngeal cavities.

Example V
Cleaning Nasal and Nasopharyngeal Cavities to Prevent Snoring by an Adult and a Child A male adult had been snoring for many years. After he learned how to use the nasal cleaning system, he practiced the nasal cleaning every day. Each night after nasal cleaning, no noise was produced.

A 14-year old boy had snored for several weeks. Before he learned to use the nasal cleaning system, the examiner observed that he had swollen mucous membranes on his turbinates in both left and right nasal cavities, and that made the airway narrow. Also, several pieces of dirty matter were on the surface of the turbinates. The boy used the nasal cleaning system washed out the dirty materials and felt immediately that he could breath much easier than before. For several nights after the cleaning he did not snore.

INDUSTRIAL APPLICABILITY

Through the use of the NNC system and process of this invention, the general population now has available to it a simple and inexpensive device that may be used to clean the nasal and nasopharyngeal cavities. As mentioned previously, this will reduce viral loads and thereby reduce the spread of infection and the opportunity for the disease to reach the lower respiratory tract. The medical community and the general population will greatly benefit from the device and method disclosed herein.

Those skilled in the art will appreciate that changes and modifications may be made to the device and the methods disclosed herein without departing from the spirit and scope of the present invention as set forth in the appended claims.

What is claimed is:

1. A modular nasal and nasopharyngeal-cleaning (NNC) kit, comprising:
   a) a compressible bottle;
   b) a cap for covering said compressible bottle, said cap having a uni-directional air-flow switch and a uni-directional fluid-flow switch passing there through, said fluid-flow switch adapted for connection above said cap to a nostril fitting and adapted for connection below said cap in said bottle to a NNC solution dispensing tube;
   c) a nostril fitting adapted for releasable connection to said uni-directional fluid-flow switch;
   d) a NNC solution dispensing tube adapted for releasable connection to said uni-directional fluid-flow switch, and;
   e) a NCC cleaning solution for dispensing by said compressible bottle, wherein said NNC solution can be properly introduced to said nasal cavity by squeezing said compressible bottle.

2. A method of accomplishing nasal and nasopharyngeal-cleaning (NNC) comprising:
   a) placing a NNC solution into a compressible bottle;
   b) connecting a NNC solution dispensing tube to a bottom portion of a cap;
   c) attaching said cap to a said compressible bottle, a top portion of said cap adapted for releasable connection to one or more interchangeable nostril fittings;
   d) releasably attaching a nostril fitting to said cap;
   e) inserting said nostril fitting at least partially into at least one nostril;
   f) compressing said compressible bottle to dispense said NNC solution into said at least one nostril, and;
   g) removing said nostril fitting from said at least one nostril.

3. The method of claim 2, wherein the steps of NNC are performed as in the order the steps are written.

4. The method of claim 2, wherein each of said nostril fittings is disposable.

5. The method of claim 2, wherein each of said nostril fittings is re-useable.

6. The method of claim 2, wherein said NNC solution, said compressible spray bottle, said NNC solution dispensing tube, and said nostril fitting, is sold together as a kit.

7. A modular nasal and nasopharyngeal-cleaning (NNC) kit, comprising:
   a) a compressible bottle for containing and dispensing a NNC solution;
   b) a NNC solution for placement in said bottle;
   c) a cap adapted for attachment to said bottle, said cap having a uni-directional air-flow switch and a uni-directional fluid-flow switch passing there through;
   d) a cleaning solution dispensing tube for attachment to a first end of said uni-directional fluid-flow switch, such that said cleaning solution dispensing tube is in communication with said cleaning solution when cap is installed to said bottle; and
   e) a nostril fitting adapted for attachment to a second end of said uni-directional fluid-flow switch, such that said nostril fitting resides above said cap when said cap is installed to said bottle;
   wherein, once assembled, compression of said bottle causes said NNC solution to pass from said bottle, through said cleaning solution dispensing tube and said uni-directional fluid-flow switch, and out of said nostril fitting; and wherein upon cessation of compression of said bottle, air re-enters and re-inflates said bottle through said uni-directional air-flow switch.

* * * * *

UNITED STATES PATENT AND TRADEMARK OFFICE
CERTIFICATE OF CORRECTION

PATENT NO.   : 6,736,792 B1                                                                 Page 1 of 1
DATED        : May 18, 2004
INVENTOR(S)  : James Liu It is certified that error appears in the above-identified patent and that said Letters Patent is hereby corrected as shown below:

Column 2,
Line 9, please delete "passed" and insert -- pressed --.

Column 4,
Line 25, please delete "honoring" and insert -- snoring --.

Column 5,
Line 25, please delete "preview" and insert -- view --.

Column 10,
Line 54, please delete "get any" and insert -- feel any --.

Signed and Sealed this

Twenty-seventh Day of July, 2004

JON W. DUDAS
*Acting Director of the United States Patent and Trademark Office*